United States Patent [19]

Baldwin et al.

[11] 4,374,140

[45] Feb. 15, 1983

[54] 2-SUBSTITUTED PROPOXY-3-CYANO-5-HYDROXYPYRIDINES AND USE AS ANTIHYPERTENSIVES

[75] Inventors: John J. Baldwin, Gwynedd Valley; Gerald S. Ponticello, Lansdale; Stanley Vickers, Perkasie, all of Pa.; Alfred Steuerwald, Orbis, Fed. Rep. of Germany

[73] Assignee: Merck & Co., Inc., Rahway, N.J.

[21] Appl. No.: 233,275

[22] Filed: Feb. 10, 1981

Related U.S. Application Data

[63] Continuation of Ser. No. 80,812, Oct. 1, 1979, abandoned.

[51] Int. Cl.³ .................... A61K 31/44; C07D 213/84
[52] U.S. Cl. .................................. 424/263; 546/288; 546/316; 546/318; 546/286; 546/298; 546/290; 546/345

[58] Field of Search ............... 546/288, 316, 318, 286, 546/298, 290, 345; 424/263

[56] References Cited

U.S. PATENT DOCUMENTS 3,983,126  9/1976  Dufour ............................... 546/298
4,115,575  9/1978  Frei et al. .......................... 546/288

OTHER PUBLICATIONS

O. Brennen, CA 31:5361-1, vol. 31.
Schroeder, CA 79:78625h, vol. 79.
Weis, C. D., CA 84:164696s, vol. 84.

Primary Examiner—Henry R. Jiles
Assistant Examiner—Robert C. Whittenbaugh
Attorney, Agent, or Firm—Daniel T. Szura; Harry E. Westlake, Jr.

[57] ABSTRACT

The present application discloses certain 2-substituted propoxy-3-cyano-5-hydroxypyridines. The compounds have pharmaceutical activity e.g. as antihypertensives.

7 Claims, No Drawings

2-SUBSTITUTED PROPOXY-3-CYANO-5-HYDROXYPYRIDINES AND USE AS ANTIHYPERTENSIVES

This is a continuation of application Ser. No. 080,812, filed Oct. 1, 1979, now abandoned.

BACKGROUND OF THE INVENTION

The present invention concerns 2-substituted propoxy-3-cyano-5-hydroxypyridines having pharmaceutical utility.

Disubstituted pyridines having pharmaceutical activity are disclosed in U.S. Pat. Nos. 4,000,282 and 4,125,618. Trisubstituted pyridines having pharmaceutical utility are generally disclosed in U.S. Pat. No. 4,115,575 and EPO publication No. 0,003,278.

Pharmaceutically active specific trisubstituted pyridines of the present invention have been discovered having useful pharmacological properties.

SUMMARY OF THE INVENTION

3-Cyano-5-hydroxy-2-(3-$C_{3-4}$alkylamino-hydroxy-propoxy)-pyridines, their salts and pharmaceutical use.

DESCRIPTION OF THE PREFERRED EMBODIMENTS

An embodiment of the invention is compounds of the formula

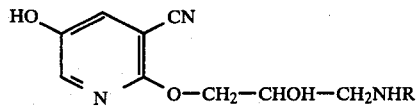

and pharmaceutically acceptable salts thereof wherein R is isopropyl or t-butyl.

The pharmaceutically acceptable salts are the acid addition salts of the formula I amines. Useful acids for salt formulation include organic as well as inorganic acids. Suitable organic acids are the carboxylic acids having from 2-24 carbon atoms such as fumaric acid, pamoic acid, acetic acid, oxalic acid, maleic acid, succinic acid, pivalic acid, isovaleric acid, lauric acid, tetracosanoic acid, tridecanoic acid, pelargonic acid, tartaric acid, citric acid and the like as well as noncarboxylic acids such as isethionic acid, naphthalenedisulfonic acid and the like. Suitable inorganic acids are exemplified by sulfuric acid, phosphoric acid, the hydrohalides such as HCl, HBr, and HI and the like.

The chiral center at the 2-propoxy prosition confers optical activity on the formula I compounds. The present compounds of formula I thus include the individual isomers, mixtures thereof as well as racemates. The symbols used to designate the isomers include − and +, 1 and d, L and D, S and R or combinations thereof. Where no specific isomer is designated, all isomers, mixtures thereof and racemates are included. Generally, the S-isomer is preferred.

Preferred compounds of formula I are those where R is t-butyl.

The compounds of formula I have pharmacological activity. The compounds are β-adrenergic blocking agents. The compounds also have antihypertensive activity of immediate onset. The compounds are thus useful to treat hypertension in animals, especially humans.

In treating hypertension in human patients, the daily dosage will range from about 1 mg. to about 1000 mg.; preferably from about 10 mg. to about 800 mg. daily; and more preferably from about 10 mg. to about 800 mg. daily; and more preferably from about 50 mg. to about 500 mg. per day.

The compound may be administered by any convenient route e.g. orally, parenterally, intramuscularly and the like using pharmaceutical compositions in a suitable dosage form e.g. tablets, elixirs, solutions or suspensions for oral administration and in sterile solutions for parenteral administration, and the like. These pharmaceutical compositions are prepared using conventional preparation procedures and can contain pharmaceutically acceptable compounding ingredients i.e. diluents, carriers, where required. These pharmaceutical compositions comprise another embodiment of the present invention.

The compounds of Formula I may be prepared by any convenient method. An especially useful process features the coupling of an appropriately substituted oxazolidine with an appropriately substituted 2-halopyridine followed by hydrolysis. This general reaction sequence is known, see e.g. U.S. Pat. No. 4,000,282.

The preparation of the appropriately substituted pyridine is carried out via a series of reactions beginning with the known 5-amino-2-chloro-3-methylpyridine. A number of intermediate compounds are prepared in this sequence. These intermediate compounds are represented by the formula

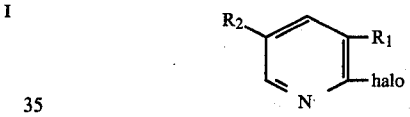

where halo is Br or Cl, preferably Cl, $R_1$ is

$CH_3$, —COOH or CN, preferably CN and $R_2$ is $CH_3O$, benzyloxy, F or OH, preferably OH.

The following example illustrates the preparation of the Formula I and II compounds. All the temperatures are °Celsius.

EXAMPLE 1

(A) Preparation of 2-chloro-5-hydroxy-3-methylpyridine and 2-chloro-5-fluoro-3-methylpyridine To a solution of 5-amino-2-chloro-3-methylpyridine (26.3 g, 0.18 mol) in 12 N HCl (90 mLO and $H_2O$ (157 mL) cooled at −10° C. to 0° C. was added dropwise a solution of $NaNO_2$ (13.9 g, 0.20 mol) in $H_2O$ (28 mL). After the addition the solution was stirred for 10 minutes and then 65% $HPF_6$ (90 mL) was added. The resulting mixture was filtered, washed with cold $H_2O$, methanol and $Et_2O$ to yield 61.7 g of diazonium salt, mp 104°-5° C. dec. The solid was cautiously added through Gooch tubing to AcOH (425 mL) preheated to 105° C. The addition was carried out over 1 hour with noticeable evolution of $N_2$. The solution was concentrated and the residue stirred for 1 hour with 10% NaOH solution (510 mL). The aqueous solution was extracted with $Et_2O$ (3X), neutralized with concentrated HCl and extracted with $CHCl_3$ (3X). After concentration, the residue was crystallized from methanol/ligroin to yield 14.5 g (56%) of 2-chloro-5-hydroxy-3-methylpyridine, mp 128°–30° C. A second crop weighing 2.24 g (8%), mp 126°–8° C., was recovered from the mother liquor; $^1$H NMR (CDCl$_3$) δ 2.35 (3H, s), 7.15 (1H, d, J=3), 7.9 (1H, d, J=3) and 9.4 (1H, bs, exch).

The Et$_2$O layer (vide supra) was dried, filtered and concentrated. The residue was sublimed at 60° C. (1.6 mm) to yield 2.15 g (8%) of 2-chloro-5-fluoro-3-methyl-pyridine, mp 38°–40° C.; $^1$H NMR (CFCl$_3$) +129.95 ppm (1F, d, J=9). The exact mass was 147.0062 (Calcd 147.0065).

(B) Preparation of 2-chloro-5-methoxy-3-methylpyridine

Into a flame dried flask under N$_2$ was placed DMF (150 mL), NaH (50% oil dispersion, 4.0 g, 0.08 mol) and 2-chloro-5-hydroxy-3-methylpyridine (11.7 g, 0.08 mol). The solution was stirred at 0°–5° C. until the evolution of H$_2$ ceased and then a solution of CH$_3$I (5.6 mL, 0.09 mol) in DMF (50 mL) was added dropwise. After the addition, the solution was allowed to stir at room temperature overnight. The resulting slurry was added to H$_2$O and extracted with Et$_2$O (3X). The organic layer was concentrated and the residue distilled at 85° C. (0.6 mm) to yield 12.8 g of 2-chloro-5-methoxy-3-methylpyridine (95%) as an oil; $^1$H NMR (CDCl$_3$) δ 2.35 (3H, s), 3.8 (3H, s), 7.1 (1H, d, J=3) and 7.9 (1H, d, J=3 ); MS m/e (M$^+$) 157.

(C) Preparation of 2-chloro-5-methoxynicotinic Acid

A mixture of 2-chloro-5-methoxy-3-methylpyridine (5.0 g, 0.031 mol), H$_2$O (400 mL) and KMnO$_4$ (18.8 g, 0.12 mol) was heated at reflux for 1 hour. The resulting mixture was then filtered hot through super-cel, cooled and extracted with CH$_2$Cl$_2$ (3X). The organic layer was dried, filtered and concentrated to yield 1.1 g of recovered 2-chloro-5-methoxy-3-methylpyridine. The aqueous layer was acidified with 12 N HCl concentrated to a small volume. The solid filtered recrystallized from iso-PrOH/Et$_2$O to yield 1.6 g (35%) of 2-chloro-5-methoxynicotinic acid, mp 169°–70° C.; $^1$H NMR (DMSO-d$_6$) δ 3.95 (3H, s), 7.85 (1H, d, J=3) and 8.3 (1H, d, J=3); IR (nujol) 1740 cm$^{-1}$.

(D) Preparation of 2-chloro-5-methoxynicotinamide

A solution of 2-chloro-5-methoxynicotinic acid (10.6 g, 0.06 mol) and SOCl$_2$ (140 mL) was heated to reflux for 3 hours. The resulting solution was concentrated and then added to cold (0°–4° C.) aqueous NH$_3$ (1 L). After stirring for 15 minutes, the reaction mixture was concentrated and the residue extracted with hot H$_3$CCN (3X). The hot H$_3$CCN solution was filtered and concentrated and to yield 10.6 g (99%) of 2-chloro-5-methoxynicotinamide, mp 129°–32° C.; $^1$H NMR (CDCl$_3$) δ 3.85 (3H, s) 6.6 (2H, bs, exch.), 7.7 (1H, d, J=3) and 8.1 (1H, d, J=3) and 8.1 (1H, d, J=3); IR (nujol) 3330 and 1650 cm$^{-1}$.

(E) Preparation of 2-chloro-5-methoxynicotinonitrile

Into a flame dried flask under N$_2$ was placed triphenylphosphine oxide (12.0 g, 0.04 mol) and CH$_2$Cl$_2$ (50 mL) and the mixture cooled to 0°–4° C. A solution of triflic anhydride (6.75 ml, 0.04 mol) in CH$_2$Cl$_2$ (80 mL) was added dropwise. After the addition, the solution was stirred for 15 min. and 2-chloro-5-methoxynicotinamide (8.0 g, 0.04 mol) was added portionwise over 15 minutes. The mixture was allowed to warm to room temperature with stirring overnight, poured into saturated Na$_2$CO$_3$ solution and extracted with CHCl$_3$ (2X). After concentration, the residue was chromatographed on silica gel and the product eluted with CHCl$_3$ to yield 6.2 g (86%) of 2-chloro-5-methoxynicotinonitrile $^1$H NMR (CDCl$_3$) δ 3.9 (3H, s), 7.5 (1H, d, J=3) and 8.3 (1H, d, J=3); (nujol) 2250 cm$^{-1}$.

(F) Preparation of 2-chloro-5-hydroxynicotinonitrile

A mixture of 2-chloro-methoxynicotinonitrile (3.1 g, 0.018 mol) and C$_5$H$_5$N HCl (90 g) was heated at 200° C. with stirring until evolution of gases ceased. After 2 hours, the solution was poured into ice and extracted with Et$_2$O (3X). The organic layer was dried, filtered, and concentrated to yield 2.0 g (70%) of 2-chloro-5-hydroxynicotinonitrile. An analytical sample of 3-chloro-5-hydroxynicotinonitrile was prepared by recrystallization from H$_2$, mp 182°–4° C.; $^1$H NMR (DMSO-d$_6$) δ 7.65 (1H, d, J=3), 8.0 (1H, d, J=3) and 8.7 (1H, bs, exch); IR (nujol) 2230 cm$^{-1}$; MS m/e M$^+$154.

(G) Preparation of 5-benzyloxy-2-chloronicotinonitrile

To a flame dried flask under N$_2$ was placed 2-chloro-5-hydroxynicotinonitrile (2.0 g, 0.012 mol), DMF (60 mL), NaH (50% oil dispersion, 0.75 g, 0.013 mol) and the mixture cooled to 0°–4° C. A solution of benzyl bromide (1.5 mL, 0.013 mol) in DMF (2 mL) was then added and the solution allowed to stir at room temperature overnight. The mixture was poured into H$_2$O and extracted with Et$_2$O (3X). The organic layer was concentrated to yield 2.0 g (100%) of 5-benzyloxy-2-chloronicotinonitrile. An analytical sample of 5-benzyloxy-3-chloronicotinonitrile was prepared by trituration with C$_6$H$_{14}$, mp 114°–15° C.; $^1$H NMR (CDCl$_3$) δ 5.2 (2H, s) 7.4 (5H, s), 7.5 (1H, d, J=3) and 8.35 (1H, d, J=3); IR (nujol) 2220 cm$^{-1}$; MS m/e M$^+$244.

(H) Preparation of (S) 5-benzyloxy-2-(3-tert-butylamino-2-hydroxypropoxy)-nicotinonitrile maleate salt To a flame dried flask under N$_2$ was placed DMF (100 mL), (S)-2-phenyl-3-tert-butyl-5-hydroxymethyloxazolidine, (2.5 g, 0.01 mol) and NaH (50% oil dispersion, 0.5 g, 0.01 mol). The mixture was heated at 90° C. for 10 minutes, then cooled to 35° C. and a solution of 5-benzyloxy-2-chloronicotinonitrile (2.5 g, 0.01 mol) in DMF (25 mL) was added dropwise and allowed to stir at room temperature overnight. The mixture was poured into H$_2$O and extracted with Et$_2$O (3X). The organic layer was dried, filtered and concentrated. The residue was treated with 1 N HCl (150 mL) and heated on a steam bath. After 15 minutes, the aqueous solution was cooled, extracted with Et$_2$O (2X), poured into saturated Na$_2$CO$_3$ solution and extracted with CH$_2$Cl$_2$ (3X). After concentration, the residue was crystallized as the maleate salt from isoPrOH/Et$_2$O to yield 3.3 g (70%) of (S)-5-benzyloxy-2-(3-tert-butylamino-2-hydroxypropoxy)nicotinonitrile maleate mp 124°–6° C.; $^1$H NMR (DMSO-d$_6$) δ 1.3 (9H, s), 3.1 (2H, m), 4.2 (3H, m), 5.2 (2H, s), 6.05 (2H, s, olefinic protons of maleic acid), 7.4 (5H, bs), 8.1 (1H, d, J=3) and 8.25 (1H, d, J=3).

(I) Preparation of (S) 2-(3-tert-butylamino-2-hydroxypropoxy)-5-hydroxynicotinonitrile (S) 5-Benzyloxy-2-(3-tert-butylamino-2-hydroxypropoxy)nicotinonitrile maleate (2.27 g, 0.005 mole) was added to saturated $Na_2CO_3$ solution and extracted with $CHCl_3$ (3X). After concentration, the residue was dissolved in EtOH (125 mL) and 10% Palladium on carbon (1.0 g) was added under $N_2$. The mixture was placed on a Herschberg hydrogenation apparatus and after 108 mL of $H_2$ was absorbed, the suspension was filtered through supercel. The solution was concentrated, the residue chromatographed on silica gel and the (S)2-(3-tert-butylamino-2-hydroxypropoxy)-5-hydroxynicotinonitrile eluted with 10% $CH_3OH$-$CHCl_3$ saturated with $NH_3$. The residue was triturated with $H_3CCN$ to yield 0.38 g (30%) of (S) 2-(3-tert-butylamino-2-hydroxypropoxy)-5-hydroxynicotinonitrile, mp 85°–90° C.; $^1H$ NMR (CDCl) δ 1.0 (9H, s), 2.55 (2H, m), 3.8 (1H, p), 4.25 (1H, d, J=6), (3H, bs, exch), 7.58 (1H, d, J=3) and 7.98 (1H, d, J=3); IR (nujol) 3300 and 2250 $cm^{-1}$. MS m/e (M-15) 250.

Claims to the invention follow.
What is claimed is:

1. Compounds of the formula

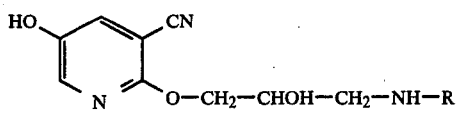

and pharmaceutically acceptable salts thereof wherein R is isopropyl or t-butyl.

2. Compound of claim 1 wherein R is isopropyl.

3. Compound of claim 2 having the S-isomer.

4. Compounds of claim 1 wherein R is t-butyl.

5. Compound of claim 4 having the S-isomer configuration.

6. A pharmaceutical composition for treating hypertension containing an effective amount of a compound of claim 1 and a diluent.

7. A method of effecting an antihypertensive response of immediate onset in humans by administering an effective amount of a composition of claim 6.

* * * * *

UNITED STATES PATENT AND TRADEMARK OFFICE
CERTIFICATE OF CORRECTION

PATENT NO. : 4,374,140
DATED : February 15, 1983
INVENTOR(S) : John J. Baldwin, et al.

It is certified that error appears in the above—identified patent and that said Letters Patent is hereby corrected as shown below:

Title page: delete "Alfred Steuerwald", listed as co-inventor

Signed and Sealed this

Nineteenth Day of July 1983

[SEAL]

Attest:

GERALD J. MOSSINGHOFF

Attesting Officer    Commissioner of Patents and Trademarks